(12) United States Patent
Duggan

(10) Patent No.: US 9,458,093 B2
(45) Date of Patent: Oct. 4, 2016

(54) COMPOSITIONS FOR THE TREATMENT OF HYPERTENSION AND/OR FIBROSIS

(71) Applicant: Vectus Biosystems Limited, Rosebery, New South Wales (AU)

(72) Inventor: Karen Annette Duggan, Clovelly (AU)

(73) Assignee: Vectus Biosystems Limited, Rosebery (AU)

( * ) Notice: Subject to any disclaimer, the term of this patent is extended or adjusted under 35 U.S.C. 154(b) by 0 days.

(21) Appl. No.: 15/022,278

(22) PCT Filed: Sep. 17, 2014

(86) PCT No.: PCT/AU2014/000923
§ 371 (c)(1),
(2) Date: Mar. 16, 2016

(87) PCT Pub. No.: WO2015/039173
PCT Pub. Date: Mar. 26, 2015

(65) Prior Publication Data
US 2016/0221933 A1    Aug. 4, 2016

(30) Foreign Application Priority Data

Sep. 17, 2013 (AU) ............................... 2013903573

(51) Int. Cl.
*C07C 235/34* (2006.01)
*A61K 31/165* (2006.01)

(52) U.S. Cl.
CPC ........... *C07C 235/34* (2013.01); *A61K 31/165* (2013.01)

(58) Field of Classification Search
None
See application file for complete search history.

(56) References Cited

U.S. PATENT DOCUMENTS

2011/0082109 A1    4/2011    Miyanaga et al.

FOREIGN PATENT DOCUMENTS

WO    2005/120545 A1    12/2005

OTHER PUBLICATIONS

Peters et al, Chemistry—A European Journal (2013), 19(7), pp. 2442-2449.*

* cited by examiner

*Primary Examiner* — Brian J Davis
(74) *Attorney, Agent, or Firm* — Wolf, Greenfield & Sacks, P.C.

(57) ABSTRACT

The present invention relates to a novel terphenyl compound and its use in the prophylactic and/or therapeutic treatment of hypertension and/or fibrosis.

16 Claims, 7 Drawing Sheets

COMPOSITIONS FOR THE TREATMENT OF HYPERTENSION AND/OR FIBROSIS

RELATED APPLICATION

This application is a national stage filing under 35 U.S.C. §371 of international application PCT/AU2014/000923, filed Sep. 17, 2014, which was published under PCT Article 21(2) in English, the contents of which are incorporated by reference herein in its entirety.

FIELD OF THE INVENTION

The present invention relates to novel compounds and their use in the prophylactic and/or therapeutic treatment of cardiovascular disease, and in particular the treatment of prehypertension, hypertension and/or fibrotic conditions.

The invention has been developed primarily for the prophylactic and/or therapeutic treatment of cardiovascular disease and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Hypertension (high blood pressure) affects 26% of the adult population worldwide with an incidence of 30-33% in western countries. The world wide incidence of hypertension is expected to reach 29% by 2025 as a consequence of the westernisation of India and China. Current studies indicate that fewer than 20% of patients with hypertension attain their recommended blood pressure (BP) target and that to achieve these targets >75% of patients require therapy with multiple antihypertensive agents. Prehypertension (slightly elevated blood pressure) affects 31% of adults in the US and may develop into hypertension if not treated.

All currently available therapies have side effects:
- Angiotensin Converting Enzyme Inhibitors (ACEI)—cough, angioneurotic oedema, hyperkalaemia;
- Angiotensin Receptor Blockers (ARB's)—angioneurotic oedema, hyperkalaemia;
- Calcium Channel Blockers (CCB)—flushing, leg/ankle oedema, constipation;
- Thiazide diuretics—new onset diabetes, gout, hyponatraemia;
- Beta (β) Blockers—new onset diabetes, inability to exercise, bradycardia, masking hypoglycemia in diabetics; and
- Aldosterone Antagonists—gynecomastia, menorrhagia, hyperkalaemia.

The need to use combination therapy increases the likelihood that patients will experience side effects and as a consequence not attain their BP target.

Hypertension and prehypertension are a major factor in the development of heart, kidney and blood vessel damage, resulting in the replacement of normal functional tissue by scar tissue or fibrosis. Some of the current antihypertensive agents—ACE inhibitors, ARB's renin inhibitors and aldosterone antagonists are able to slow the progression of the replacement of functional tissue by fibrosis, none have been shown to reverse existing fibrosis and restore normal tissue architecture. There is thus a need for agents which have the efficacy to reduce BP significantly and thus enable a larger proportion of patients to attain BP target with single agent therapy and/or to reverse existing fibrosis and/or restore normal tissue architecture.

It is an object of the present invention to overcome or ameliorate at least one of the disadvantages of the prior art, or to provide a useful alternative.

SUMMARY OF THE INVENTION

Surprisingly, the present inventors have found that certain novel terphenyl compounds have blood pressure lowering and/or anti-fibrotic effects. These effects may be seen in intravenous and/or oral dosing studies.

According to one aspect, the present invention provides a compound of the formula

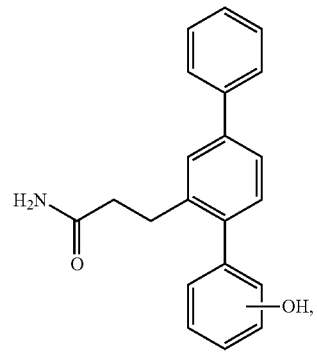

or a stereoisomer or pharmaceutically acceptable salt thereof.

In one embodiment, the compound is (VB0004)

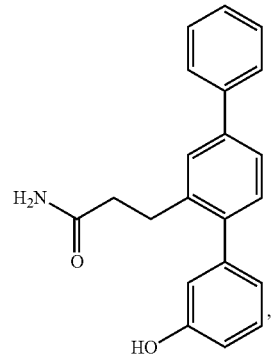

or a stereoisomer or pharmaceutically acceptable salt thereof.

According to another aspect, the present invention relates to a pharmaceutical composition comprising a compound of the present invention and a pharmaceutically acceptable excipient.

According to another aspect, the present invention relates to a method for the therapeutic treatment of hypertension or prehypertension in a subject comprising administering to the subject a compound according to the present invention.

According to another aspect, the present invention relates to a method for the therapeutic treatment of fibrosis in a subject comprising administering to the subject a compound according to the present invention.

According to another aspect, the present invention relates to a method for the prophylactic treatment of fibrosis in a subject comprising administering to the subject a compound according to the present invention.

According to another aspect, the present invention relates to a method for the therapeutic treatment of hypertension and fibrosis in a subject comprising administering to the subject a compound according to the present invention.

According to another aspect, the present invention relates to a method for the therapeutic treatment of prehypertension and fibrosis in a subject comprising administering to the subject a compound according to the present invention.

In one embodiment, the fibrosis is myocardial fibrosis or kidney fibrosis.

In another embodiment, the fibrosis is myocardial fibrosis and kidney fibrosis.

According to another aspect, the present invention relates to a compound of the present invention for use in the therapeutic treatment of hypertension or prehypertension.

According to another aspect, the present invention relates to a compound of the present invention for use in the therapeutic treatment of fibrosis.

According to another aspect, the present invention relates to a compound of the present invention for use in the prophylactic treatment of fibrosis.

According to another aspect, the present invention relates to a compound of the present invention for use in the therapeutic treatment of hypertension and fibrosis.

According to another aspect, the present invention relates to a compound of the present invention for use in the therapeutic treatment of prehypertension and fibrosis.

According to another aspect, the present invention relates to use of a compound of the present invention for the manufacture of a medicament for the therapeutic treatment of hypertension or prehypertension.

According to another aspect, the present invention relates to use of a compound of the present invention for the manufacture of a medicament for the therapeutic treatment of fibrosis.

According to another aspect, the present invention relates to use of a compound of the present invention for the manufacture of a medicament for the prophylactic treatment of fibrosis.

According to another aspect, the present invention relates to use of a compound of the present invention for the manufacture of a medicament for the therapeutic treatment of hypertension and fibrosis.

According to another aspect, the present invention relates to use of a compound of the present invention for the manufacture of a medicament for the therapeutic treatment of prehypertension and fibrosis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
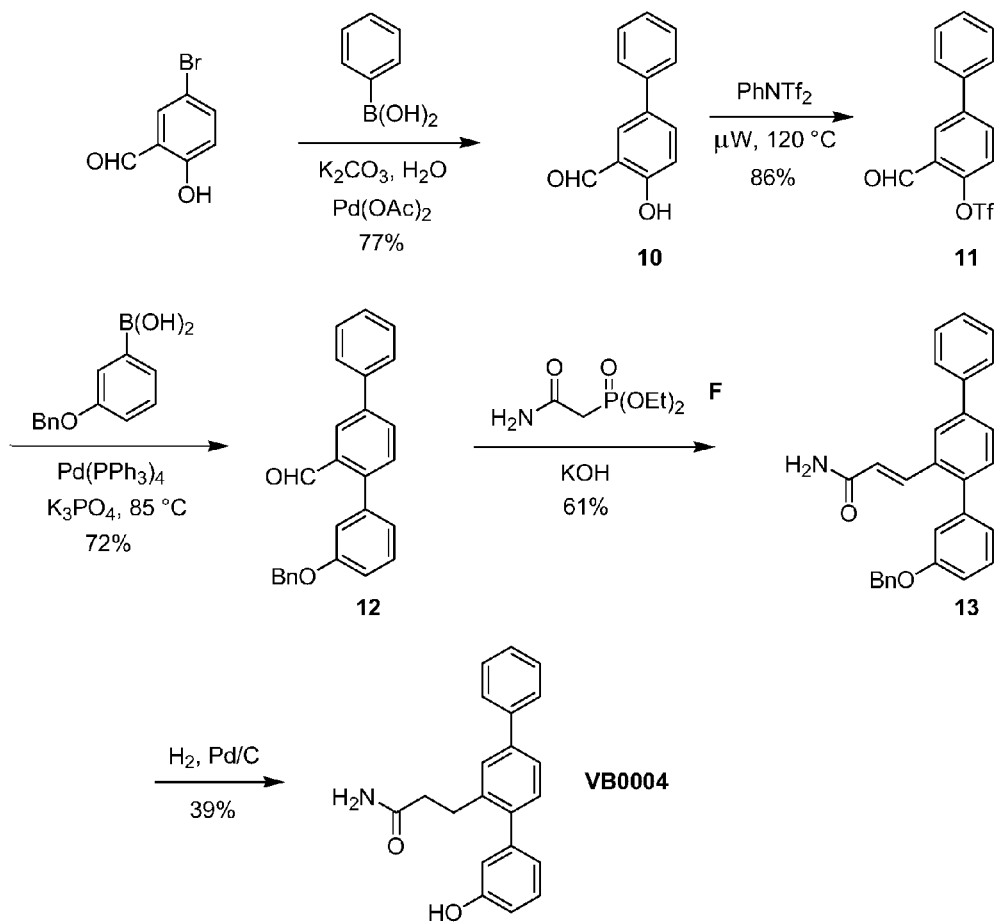
FIG. 1: Synthesis of VB0004.

The present invention relates to certain novel terphenyl compounds that show blood pressure lowering and anti-fibrotic effects in intravenous and/or oral dosing studies in an experimental animal model. With respect to anti-fibrotic activity, the compounds of the present invention are effective in preventing fibrosis, slowing down progression of established fibrosis and/or reducing the degree (reversal) of established fibrosis. These are important findings with respect to the range and severity of conditions which can be treated with the compounds of the present invention.

The compounds of the present invention are represented by the formula:

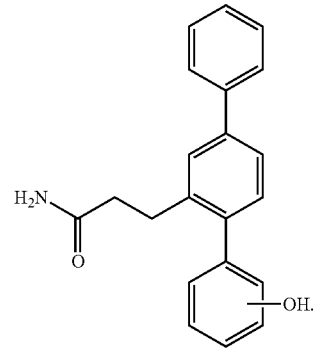

The following compound is a specific, but non-limiting, example of the compounds of the present invention:

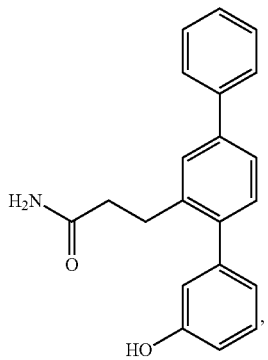

(VB0004)

The compound may also be represented by the following name: 2'-[3-hydroxy-(1,1':4',1''-terphenyl)]propanamide.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The term "fibrosis" as used in the context of the present invention includes, but is not limited to, myocardial fibrosis and/or kidney fibrosis.

In addition to treatment of established fibrosis, the compounds of the present invention may be used prophylactically in subjects at risk of developing fibrosis. As an example of subjects in the risk category for developing fibrosis are those having hypertension, diabetes, myocarditis, ischaemic heart disease, Conn's Syndrome, pheochromocytoma, genetic predisposition high salt diet and/or receiving drugs used in cancer chemotherapy (such as daunorubicin). The term "prophylactic" as used in the context of the present invention is intended inter alia to encompass treatments used to prevent or slow down the development of fibrosis in the at risk group. Subjects who may be given prophylactic treatment may already have signs of early heart failure on echocardiography.

The term "hypertension" as used in the context of the present invention indicates an adult blood pressure of above about 139 mmHg systolic and/or above about 89 mmHg diastolic.

The term "prehypertension" as used in the context of the present invention indicates an adult blood pressure in the range about 120-139 mmHg systolic and/or about 80-89 mmHg diastolic.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

When the compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1

Compound Synthesis

Synthesis Summary

The synthetic route used to prepare VB0004 is shown in FIG. 1. Briefly, 5-phenylsalicylaldehyde (10) was prepared by a Suzuki cross-coupling reaction between 5-bromosalicylaldehyde and phenylboronic acid. This phenol was then converted to the corresponding aryl triflate (11) (using N-phenyltriflimide and microwave irradiation), which underwent another Suzuki reaction with 3-(benzyloxy)phenylboronic acid to form terphenyl aldehyde (12). A Horner-Wadsworth-Emmons reaction between aldehyde (12) and phosphonate (F) afforded α,β-unsaturated amide (13), which was subsequently reduced to form VB0004.

Figure 2:
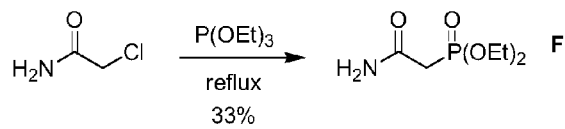
FIG. 2: Synthesis of diethyl carbamoylmethylphosphonate.

Diethyl carbamoylmethylphosphonate (F) was generated from an Arbuzov reaction between 2-chloroacetamide and triethyl phosphite (prepared as shown in FIG. 2).

Synthesis of 2-Hydroxy-5-phenylbenzaldehyde (10)

5-Bromosalicylaldehyde (2.49 g, 12.4 mmol), phenyl boronic acid (1.51 g, 12.4 mmol), palladium(II) acetate (14 mg, 0.5 mol %) and potassium carbonate (5.14 g, 37.2 mmol) were stirred in degassed water (75 mL) at ambient temperature for 2 h, under an argon atmosphere. The reaction was monitored by TLC (1:1 dichloromethane/pentane). Water (75 mL) was added and the reaction mixture acidified (pH 6) with 10% HCl, then extracted with ethyl acetate (3×). The combined organic extracts were washed with brine, then dried and concentrated. The crude material was passed through a short column of silica, eluting with 1:1 dichloromethane/pentane, then recrystallised from ethyl acetate/pentane to afford 2-hydroxy-5-phenylbenzaldehyde (1.89 g, 77%) as dark yellow crystals (can be triturated with pentane instead recrystallised if desired); mp 100-101° C. $^1$H NMR (400 MHz, CDCl$_3$) δ 10.99 (s, 1H); 9.97 (s, 1H); 7.78-7.73 (m, 2H); 7.56-7.52 (m, 2H); 7.47-7.41 (m, 2H); 7.37-7.32 (m, 1H); 7.09-7.04 (m, 1H). $^{13}$C NMR (100 MHz, CDCl$_3$) δ 196.9, 161.2, 139.6, 136.0, 133.6, 132.1, 129.2, 127.6, 126.8, 121.0, 118.4. EIMS: m/z 198 [M]$^+$. HRMS calcd for C$_{13}$H$_{10}$O$_2$ 198.0675. found 198.0677.

Synthesis of 3-Formylbiphenyl-4-yl-trifluoromethanesulfonate (11)

2-Hydroxy-5-phenylbenzaldehyde (100 mg, 0.50 mmol), N-phenyltriflimide (180.0 mg, 0.51 mmol) and potassium carbonate (209 mg, 1.51 mmol) were stirred in dry THF in a sealed tube, and heated at 120° C. for 6 min, using microwave irradiation. The solvent was removed under reduced pressure; water and dichloromethane were added and the layers separated. The aqueous layer was extracted further with dichloromethane (2×). The combined organic extracts were washed with brine (1×), then dried and concentrated. Purified by radial chromatography, eluting with 1:1 dichloromethane/pentane, to afford 3-formylbiphenyl-4-yl-trifluoromethanesulfonate (143 mg, 86%) as a clear, colourless oil. $^1$H NMR (200 MHz, CDCl$_3$) δ 10.32 (s, 1H); 8.17 (d, 1H, J=2.4 Hz); 7.89 (dd, 1H, J=8.6, 2.5 Hz); 7.63-7.36 (m, 6H). $^{13}$C NMR (125 MHz, CDCl$_3$) δ 186.5, 149.1, 142.3, 138.0, 134.1, 129.2, 129.1, 128.8, 128.6, 127.2, 122.9, 118.7 (q, J$_{CF}$=320.9 Hz). $^{19}$F NMR (188 MHz, CDCl$_3$) δ −73.2. EIMS: m/z 330 [M]$^+$. HRMS calcd for C$_{14}$H$_9$F$_3$O$_2$S, 330.0168. found 330.0163.

Synthesis of 2'-[3-Benzyloxy-(1,1':4',1''-terphenyl)] carbaldeyde (12)

3-Formylbiphenyl-4-yl-trifluoromethanesulfonate (153 mg, 0.463 mmol), 3-benzyloxyphenylboronic acid (116 mg, 0.51 mmol), tetrakis(triphenylphosphine)palladium(0) (13 mg, 2.5 mol %) and anhydrous potassium phosphate (147 mg, 0.695 mmol) were placed in a Schlenk flask, under an argon atmosphere. Degassed 1,4-dioxane (2 mL) was added and the mixture purged with argon. The reaction mixture was heated at 85° C. until complete conversion was observed (monitored by GCMS); generally required overnight reaction time. The reaction mixture was diluted with benzene (4 mL) and treated with 30% aqueous hydrogen peroxide (10 mL). The product was extracted with diethyl ether (3×); the combined organic extracts were washed with brine then dried and concentrated. Purified by radial chromatography, eluting with 1:1 dichloromethane/pentane, to afford 2'-[3-benzyloxy-(1,1':4',1''-terphenyl)]carbaldeyde (122 mg, 72%) as a clear, colourless, viscous oil. $^1$H NMR (400 MHz, CDCl$_3$) δ 10.02 (s, 1H); 8.24 (dd, 1H, J=2.1, 0.3 Hz); 7.86 (dd, 1H, J=8.0, 2.1 Hz); 7.68-7.64 (m, 2H); 7.56-7.30 (m, 10H); 7.08-7.02 (m, 2H); 7.01-6.97 (m, 1H); 5.11 (s, 2H). $^{13}$C NMR (100 MHz, CDCl$_3$) δ 192.6, 159.0, 144.8, 141.0, 139.7, 139.1, 136.9, 134.2, 132.2, 131.4, 129.8, 129.2, 128.9, 128.4, 128.2, 127.8, 127.3, 126.1, 123.2, 116.9, 114.9, 70.4. EIMS: m/z 364 [M]$^+$. HRMS calcd for C$_{26}$H$_{20}$O$_2$ 364.1458. found 364.1450.

Synthesis of 2'-[3-Benzyloxy-(1,1':4',1''-terphenyl)] acrylamide (13)

2'-[3-benzyloxy-(1,1':4',1''-terphenyl)]carbaldeyde (201 mg, 0.552 mmol) and diethyl(carbamoylmethyl)phosphonate (108 mg, 0.55 mmol) were dissolved in dry THF (7 mL), and added slowly to a vigorously stirred suspension of powdered potassium hydroxide (62 mg, 1.10 mmol) in THF (2 mL). The reaction was stirred at ambient temperature for 1 h, under an argon atmosphere, monitoring by TLC (1:1 dichloromethane/pentane). The THF was removed under reduced pressure, and the residue taken up in water and extracted with dichloromethane (3×). The combined organic extracts were washed with brine (1×) then dried and concentrated. Recrystallisation from ethyl acetate/pentane afforded 2'-[3-benzyloxy-(1,1':4',1''-terphenyl)]acrylamide (137 mg, 61%) as pale yellow crystals; mp 175-176° C. $^1$H NMR (400 MHz, DMSO-$d_6$) δ 7.95 (d, 1H, J=2.0 Hz); 7.78-7.22 (m, 3H); 7.55-7.31 (m, 12H); 7.17-7.07 (m, 2H); 6.99 (m, 1H); 6.92 (m, 1H); 6.79 (d, J=15.8 Hz, 1H); 5.16 (s, 2H). $^{13}$C NMR (125 MHz, DMSO-$d_6$) δ 166.5, 158.3, 140.8, 140.7, 139.8, 139.4, 137.5, 137.0, 133.2, 130.9, 129.5, 129.1, 128.5, 127.9, 127.8, 127.8, 127.6, 126.8, 124.5, 123.8, 122.2, 115.9, 114.0, 69.4. EIMS: m/z 405 [M]$^+$. HRMS calcd for $C_{28}H_{23}NO_2$ 405.1723. found 405.1714.

Synthesis of 2'-[3-Hydroxy-(1,1':4',1''-terphenyl)] propanamide (VB0004)

2'-[3-Benzyloxy-(1,1':4',1''-terphenyl)]acrylamide (740 mg, 1.82 mmol) and 10% palladium on carbon catalyst (100 mg) were stirred at ambient temperature for 20 h, under a hydrogen atmosphere. The catalyst was removed by filtration on glass filter paper followed by filtration on Celite, then concentrated. Purified by radial chromatography, eluting with 1:1 dichloromethane/pentane, followed by recrystallisation from ethyl acetate/pentane to afford 2'-[3-hydroxy-(1,1':4',1''-terphenyl)]propanamide (224 mg, 39%) as colourless crystals; mp 167.2-168.9° C. $^1$H NMR (200 MHz, DMSO-$d_6$) δ 9.52 (s, 1H); 7.77-7.15 (m, 10H); 6.87-6.65 (m, 4H); 2.84 (m, 2H); 2.31 (m, 2H). $^{13}$C NMR (50 MHz, DMSO-$d_6$) δ 173.4, 157.1, 142.1, 140.6, 140.0, 139.1, 139.1, 130.2, 129.2, 128.9, 127.4, 127.2, 126.6, 124.1, 119.6, 115.8, 114.0, 36.2, 28.2. EIMS: m/z 317 [M]$^+$. HRMS calcd for $C_{21}H_{19}NO_2$ 317.1410. found 317.1411.

Synthesis of Diethyl Carbamoylmethylphosphonate (F)

2-Chloroacetamide (5.01 g, 53.6 mmol) and triethyl phosphite (9.19 mL, 53.6 mmol) were heated at reflux in o-xylene (14 mL) for 3.5 h. The solvent was removed under reduced pressure to afford a dark brown tar-like residue. The residue was taken up in dichloromethane and filtered through a short column of silica. The filtrate was concentrated and the solid recrystallised from ethyl acetate/pentane to afford diethyl carbamoylmethylphosphonate (3.42 g, 33%) as light brown crystals. $^1$H NMR (200 MHz, DMSO-$d_6$) δ 7.35 (br s, 1H); 7.02 (br s, 1H); 4.02 (dq, 4H, J=7.1 Hz, $^3J_{PH}$=1.1 Hz); 2.80 (d, 2H, $^2J_{PH}$=21.4 Hz); 1.23 (t, 6H, J=7.0 Hz). $^{13}$C NMR (50 MHz, DMSO-$d_6$) δ 166.0 (d, $^2J_{CP}$=5.1 Hz); 61.5 (d, $^2J_{CP}$=6.0 Hz); 34.5 (d, $^1J_{CP}$=131.6 Hz); 16.2 (d, $^3J_{CP}$=6.0 Hz). $^{31}$P NMR (81 MHz, DMSO-$d_6$) 23.8. ESIMS: m/z 218 [M+Na]$^+$. HRMS calcd for $C_6H_{14}NO_4P$, 195.0655. found 195.0653.

Example 2

In Vitro Screening

The xCELLigence SP system (Roche) was used to measure changes in cellular impedance (cell index) following the treatment of A10 embryonic vascular smooth muscle cells (ATCC, CRL-1476) with VB0004. This in vitro assay was correlated with blood pressure data obtained in the animal model described below in Example 3, so that it can be used for faster screening of larger number of compounds. In this in vitro cell based experimental system a negative impedance profile correlates with blood pressure reduction in rats—a decrease in impedance is associated with vasodilatation and an increase in impedance is associated with vasoconstriction (Stallaert W, Dorn J F, van der Westhuizen E, Audet M & Bouvier M. Impedance responses reveal β-adrenergic signaling pluridensitometry and allow classification of ligands with distinct signalling profiles PLoS ONE 2012; 7(1):e29420, doi:10.1371/journal.pone.0029420).

Briefly, 50 μl of cell culture medium (DMEM low glucose supplemented with 10% fetal bovine serum at 37° C.) was added to each well of an E-Plate 96 (Roche), and the background impedance in each well was measured. 50 μl of A-10 cell suspension (10,000 cells/well) was then added to the appropriate wells of the E-Plate 96. Cell index was monitored for each well of the E-Plate 96 in RTCA SP Station within the cell culture incubator. After overnight incubation for 16-20 hours at 5% CO2 and 95% humidity, 100 μl of VB0004 solution (VB0004 was prepared in DMSO and diluted with cell culture medium to a final DMSO concentration of 0.25%) was added to the appropriate wells of the E-Plate 96 and cell index values were measured immediately following compound treatment every 20 seconds for 3 hours. Cell index value is baseline-corrected by subtracting the cell index of vehicle-treated cells and normalized by dividing by the cell index at the time point immediately before compound addition. Baseline normalized cell index as a function of time is plotted using Roche RTCA software.

Figure 3:
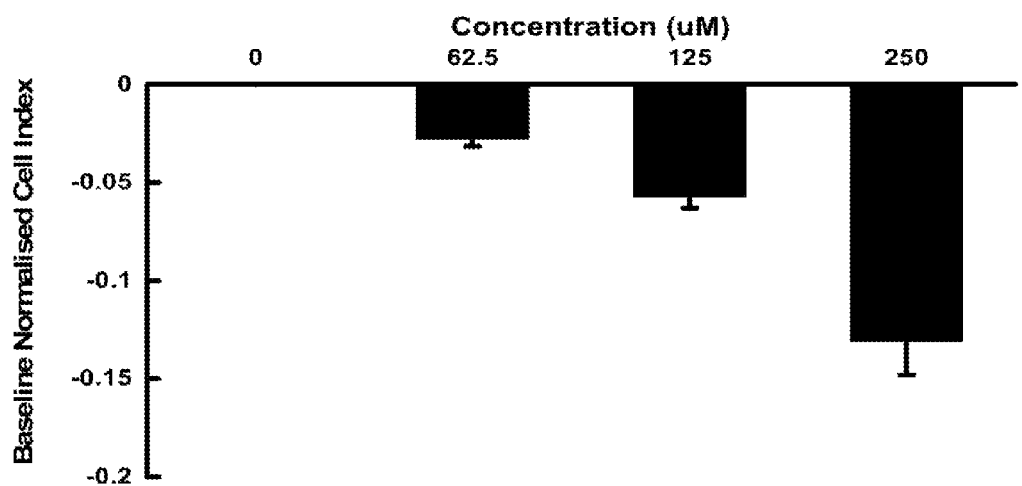
FIG. 3: Negative impedance responses were observed for compound VB0004 at a concentration of 62.5 µM, 125 µM and 250 µM when incubated with A10 vascular smooth muscle cells in a Roche xCELLIgence.

Compounds may achieve reductions in blood pressure by interaction with vascular smooth muscle cells causing these cells to relax resulting in vasodilatation and a reduction in blood pressure. These are termed direct vasodilators. The negative impedance response observed for A10 vascular smooth muscle cells treated with VB0004 at concentrations of 62.5, 125 and 250 μM (FIG. 3) demonstrates that VB0004 is a direct vasodilator. These results correlate well with mean systolic blood pressure in SHR on 2.2% salt diet after 4 weeks treatment with 10, 100 and 500 pmol/kg/min VB0004 orally (see FIG. 4 and below).

The xCELLigence SP system (Roche) was also used to measure changes in cellular impedance (cell index) following the treatment of bovine aortic endothelial cells (European Collection of Cell Cultures) with test compound. The method employed is the same for the A10 embryonic vascular smooth muscle cells described above but with the cell culture medium supplemented with 15% fetal bovine serum instead of 10%.

Figure 5:
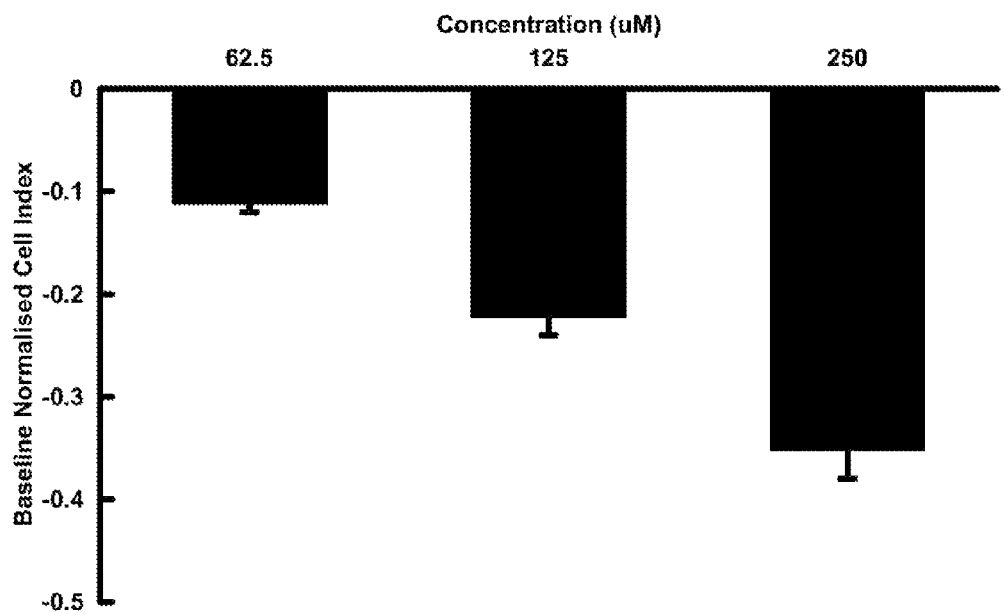
FIG. 5: Negative impedance responses were observed for compound VB0004 at a concentration of 62.5 µM, 125 µM and 250 µM when incubated with bovine aortic endothelial cells in a Roche xCELLIgence.

Compounds may interact with vascular endothelial cells causing the release of substances such as nitric oxide and endothelium-derived hyperpolarising factor, which in turn act on the vascular smooth muscle cells causing vasodilatation and lowering blood pressure. Such compounds are termed indirect vasodilators. The negative impedance response observed for bovine aortic endothelial cells treated with VB0004 at concentrations of 62.5, 125 and 250 μM (FIG. 5), demonstrates that VB0004 is also an indirect vasodilator.

Example 3

In Vivo Screening

Oral Studies

Fourteen week old SHR (on a 2.2% salt diet; Glen Forrest Stockfeeders) were randomly assigned to zero time control, VB0004 treatment (10, 100, 500, 1,000 and 2,500 pmol/kg/min) in the drinking solution or control drinking solution (5% ethanol in deionised distilled water (n=5 each group). The rats assigned to zero time control group were anaesthetised and had their heart and kidneys harvested while rats assigned to control and VB0004 treatment were weighed twice weekly and had their drinking solution intake monitored to allow adjustment of the VB0004 concentration in the drinking solution to maintain a constant dose over the 4, 6 or 8 weeks study periods. Blood pressure was measured twice weekly by tail cuff plethysmography (PowerLab, ADInstruments, Castle Hill, NSW, Australia). After 4, 6 or 8 weeks rats were anaesthetised, and their heart and kidneys harvested for quantitation of fibrosis.

Intravenous Administration

Fourteen week old SHR (on a 2.2% salt diet; Glen Forrest Stockfeeders) were randomly assigned to zero time control, VB0004 infusion (10 and 20 pmol/kg/min) or vehicle (20% DMSO in normal saline, Baxter Healthcare, Sydney NSW Australia) infusion (n=5 each group). Rats were anaesthetised and the rats assigned to zero time control group had their heart and kidneys harvested while rats assigned to VB0004 or vehicle infusion had a cannula inserted into the iliac vein which was connected to an Alzet osmotic minipump (Durect Corporation, Cupertino, Calif., USA) containing VB0004 or vehicle. Blood pressure was measured twice weekly by tail cuff plethysmography (PowerLab, ADInstruments, Castle Hill, NSW, Australia). After 4 weeks rats were again anaesthetised, their heart and kidneys harvested for quantitation of fibrosis.

Fibrosis Quantitation

To quantitate fibrosis, tissue slices ≤3 mm thick were fixed in 10% buffered formalin for 24 hours, processed and embedded in paraffin. Three micron transverse sections were stained using Masson's trichrome stain. A minimum of 20 random fields at magnification ×20 from transverse sections (5 at each of 2 levels) were digitized and the degree of fibrosis determined as a percent of field area of each digitized image using Image-Pro Plus V.5 (Media Cybernetics, Bethesda, Md., USA) then averaged to determine the level of fibrosis for tissue for each rat.

Results

Figure 4:
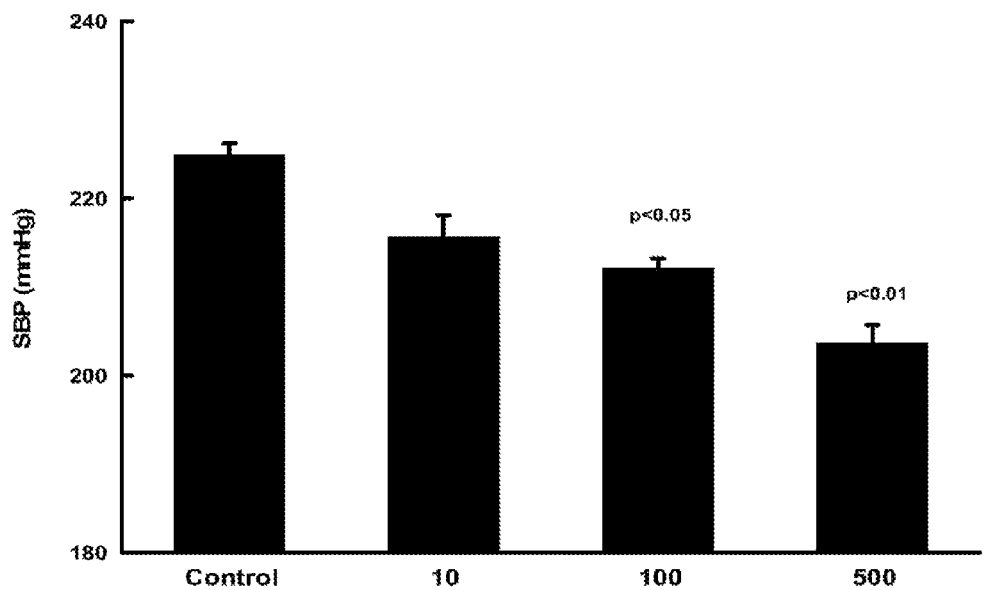
FIG. 4: Systolic blood pressures in SHR on 2.2% salt diet after 4 weeks treatment with oral administration of VB0004 at 10, 100 and 500 pmol/kg/min.

Mean systolic blood pressure in SHR on 2.2% salt diet after 4 weeks treatment with 10, 100 and 500 pmol/kg/min VB0004 orally showed decreased blood pressure compared to controls (FIG. 4).

Figure 6:
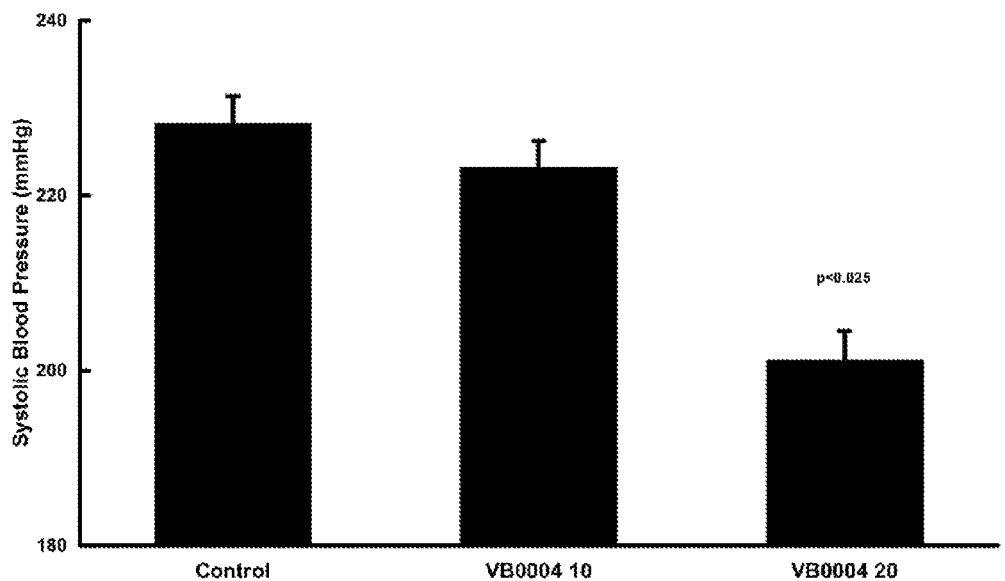
FIG. 6: Systolic blood pressures in SHR on 2.2% salt diet after 4 weeks treatment with intravenous infusion of VB0004 at 10 and 20 pmol/kg/min.

Intravenous administration of VB0004 at 10 and 20 pmol/kg/min for 4 weeks decreased SBP by 20 mmHg compared with vehicle control (FIG. 6).

Figure 7:
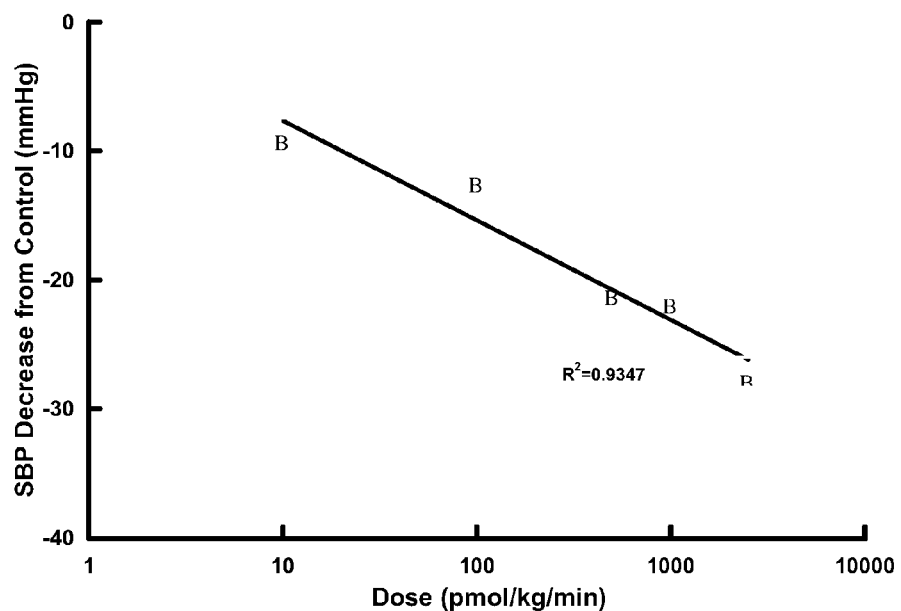
FIG. 7: Decrease in mean systolic blood pressure after 4 weeks treatment with various doses of VB0004 ranging from 10 to 2,500 pmol/kg/min orally compared with the mean systolic blood pressure of control animals.

Mean systolic blood pressure in SHR on a 2.2% salt diet treated with VB0004 at 10 to 2,500 pmol/kg/min given orally for 4 weeks showed decreased blood pressure with increased dose compared with controls (FIG. 7). As systolic blood pressure continues to decrease with increasing dose without achieving plateau no maximum dose has yet been delineated.

Figure 8:
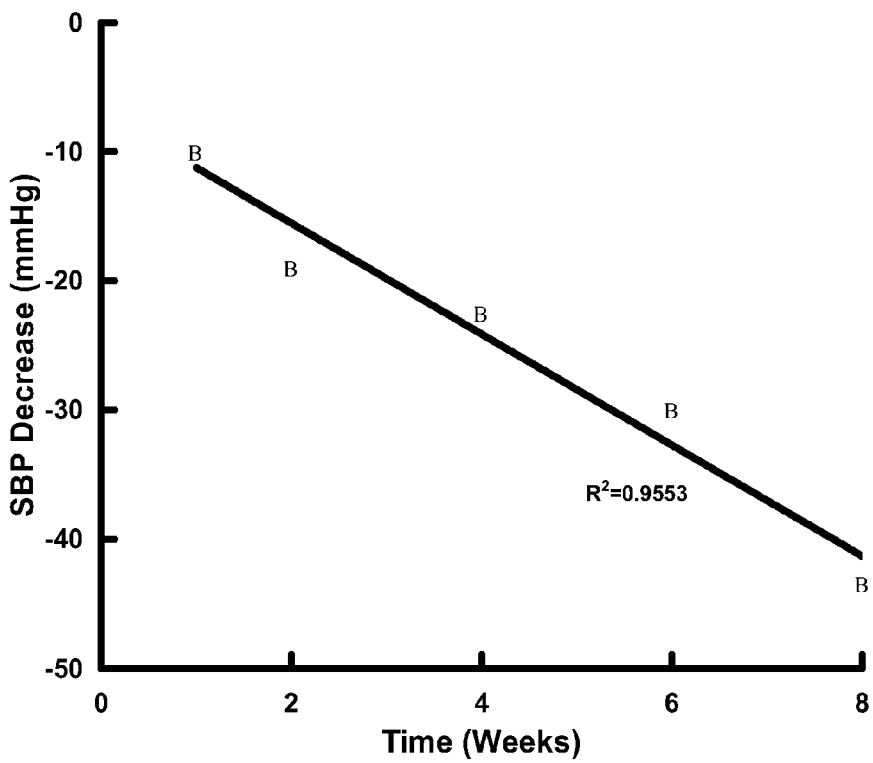
FIG. 8: Decrease in mean systolic blood pressure in SHR on a 2.2% salt diet treated with VB0004 at 2,500 pmol/kg/min orally compared with controls at various time periods up to 8 weeks.

Mean systolic blood pressure in SHR on a 2.2% salt diet treated with VB0004 at 2,500 pmol/kg/min given orally continued to decrease with time indicating that maximal effect for this dose has not yet been achieved after 8 weeks therapy (FIG. 8).

Figure 9:
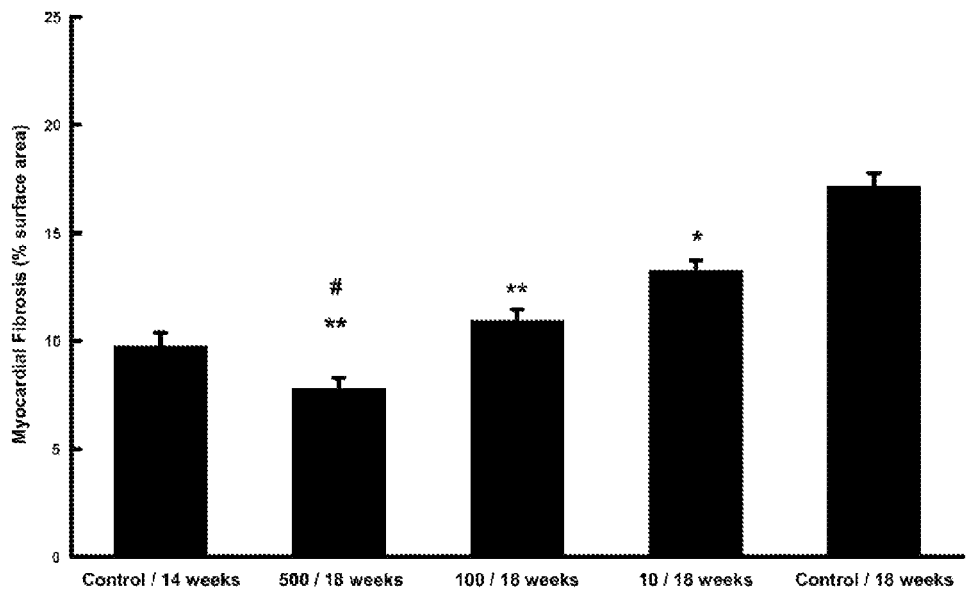
FIG. 9: Fibrosis in the heart after 4 weeks treatment with VB0004 orally in 18 week old SHR on 2.2% salt diet at doses from 10 to 500 pmol/kg/min (hatched bars) is decreased compared with fibrosis in 14 and 18 week controls (open bars) in SHR on 2.2% salt diet. * p<0.005, ** p<0.0005 vs 18 week control, # p<0.05 vs 14 week control.

Fibrosis in the heart after 4 weeks treatment with VB0004 orally in 18 week old SHR on 2.2% salt diet at doses from 10 to 500 pmol/kg/min (hatched bars) decreased compared with fibrosis in 14 and 18 week controls (open bars) in SHR on 2.2% salt diet (FIG. 9).

Figure 10:
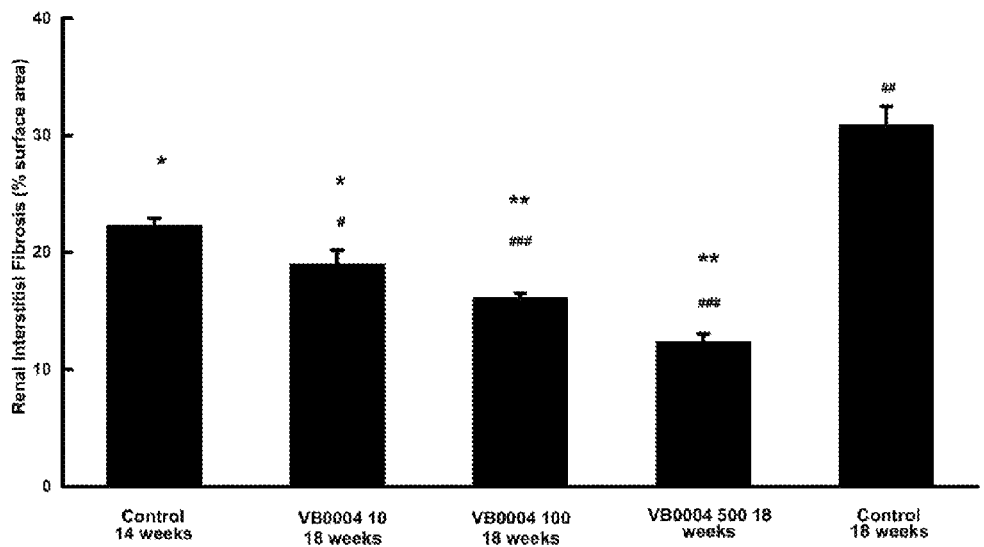
FIG. 10: Fibrosis in the kidney after 4 weeks treatment with VB0004 orally in 18 week old SHR on 2.2% salt diet at doses from 10 to 500 pmol/kg/min (hatched bars) is decreased compared with fibrosis in 14 and 18 week controls (open bars) in SHR on 2.2% salt diet. * p<0.005, ** p<0.0005 vs 18 week control, # p<0.05, ## p<0.005, ### p<0.0005 vs 14 week control.

Fibrosis in the kidney after 4 weeks treatment with VB0004 orally in 18 week old SHR on 2.2% salt diet at doses from 10 to 500 pmol/kg/min (hatched bars) decreased compared with fibrosis in 14 and 18 week controls (open bars) in SHR on 2.2% salt diet (FIG. 10).

Figure 11:
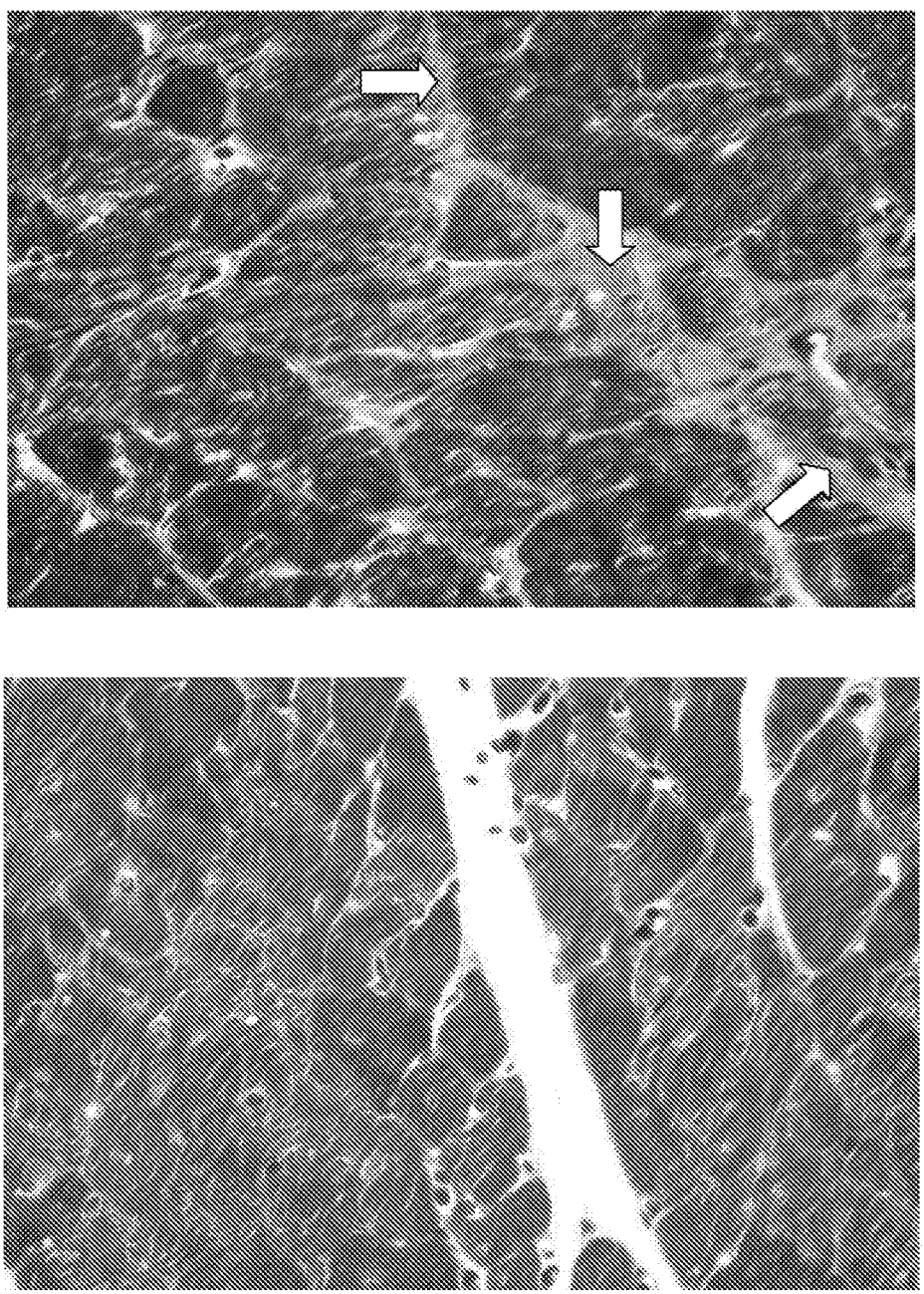
FIG. 11: Micrographs of heart from control rats and rats treated for four weeks with 500 pmol/kg/min of VB0004. Upper panel shows section from control heart where fibrous tissue appears grey in Masson's trichrome stain (see arrows). Lower panel shows that virtually no fibrous tissue is present in sections from VB0004 treated animals.

Heart from control animals (18 week old SHR on 2.2% salt diet) showed extensive fibrosis tissue (appears grey in the Masson's trichrome stain) while heart from VB0004-treated animals had virtually no fibrous tissue present (FIG. 11).

Figure 12:
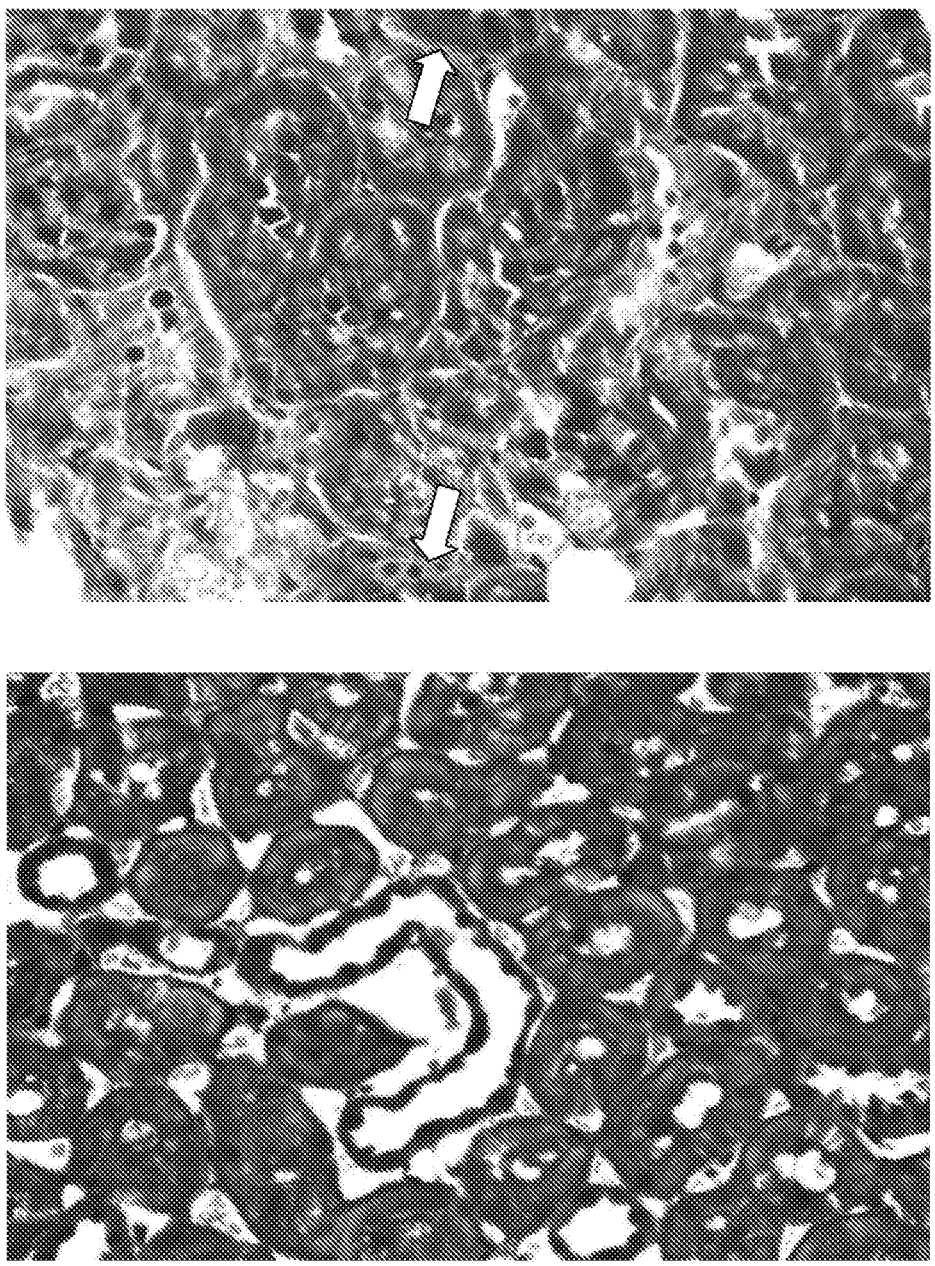
FIG. 12: Micrographs of kidney from control rats and rats treated for four weeks with 500 pmol/kg/min of VB0004. Upper panel shows section from control kidney where fibrous tissue appears grey in Masson's trichrome stain (see arrows). Lower panel shows that virtually no fibrous tissue is present in sections from VB0004 treated animals.

Kidney from control animals (18 week old SHR on 2.2% salt diet) showed extensive fibrosis tissue (appears grey in the Masson's trichrome stain) while kidney from VB0004-treated animals had virtually no fibrous tissue present (FIG. 12).

The claims defining the invention are as follows:

1. A compound of the formula

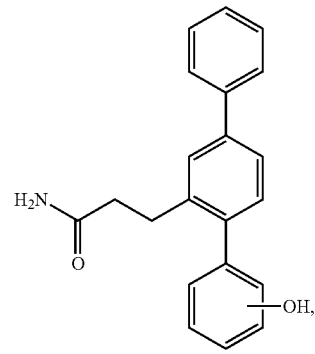

or a stereoisomer or pharmaceutically acceptable salt thereof.

2. The compound according to claim 1 wherein the compound is of the formula

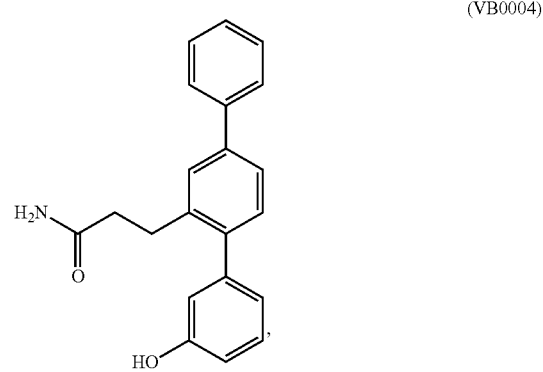 [SMILES: NC(=O)CCc1cc(-c2ccccc2)ccc1-c1cccc(O)c1]

or a stereoisomer or pharmaceutically acceptable salt thereof.

3. A pharmaceutical composition comprising a compound, or a stereoisomer or pharmaceutically acceptable salt thereof, according to claim 1 and a pharmaceutically-acceptable excipient.

4. A method for the therapeutic treatment of hypertension or prehypertension in a subject comprising administering to the subject a compound, or a stereoisomer or pharmaceutically acceptable salt thereof, according to claim 1.

5. A method for the prophylactic treatment of fibrosis in a subject comprising administering to the subject a compound, or a stereoisomer or pharmaceutically acceptable salt thereof, according to claim 1.

6. A method for the therapeutic treatment of fibrosis in a subject comprising administering to the subject a compound, or a stereoisomer or pharmaceutically acceptable salt thereof, according to claim 1.

7. A method for the therapeutic treatment of hypertension and fibrosis in a subject comprising administering to the subject a compound, or a stereoisomer or pharmaceutically acceptable salt thereof, according to claim 1.

8. A method of treating prehypertension and fibrosis in a subject comprising administering to the subject a compound, or a stereoisomer or pharmaceutically acceptable salt thereof, according to claim 1.

9. The method according to claim 5 wherein the fibrosis is myocardial fibrosis or kidney fibrosis.

10. The method according to claim 5 wherein the fibrosis is myocardial fibrosis and kidney fibrosis.

11. The method according to claim 6 wherein the fibrosis is myocardial fibrosis or kidney fibrosis.

12. The method according to claim 6 wherein the fibrosis is myocardial fibrosis and kidney fibrosis.

13. The method according to claim 7 wherein the fibrosis is myocardial fibrosis or kidney fibrosis.

14. The method according to claim 7 wherein the fibrosis is myocardial fibrosis and kidney fibrosis.

15. The method according to claim 8 wherein the fibrosis is myocardial fibrosis or kidney fibrosis.

16. The method according to claim 8 wherein the fibrosis is myocardial fibrosis and kidney fibrosis.

* * * * *